United States Patent [19]

Deniega

[11] Patent Number: 4,651,737

[45] Date of Patent: Mar. 24, 1987

[54] NONMETALLIC SURGICAL CLIP

[75] Inventor: Jose C. Deniega, Brookfield, Conn.

[73] Assignee: American Cyanamid Company, Stamford, Conn.

[21] Appl. No.: 660,757

[22] Filed: Oct. 15, 1984

[51] Int. Cl.⁴ .............................................. A61B 17/12
[52] U.S. Cl. .................................... 128/325; 128/346; 24/522; 269/166
[58] Field of Search ............... 128/325, 346, 326, 321, 128/322, 334 R, 335; 24/522, 528; 269/166

[56] References Cited

U.S. PATENT DOCUMENTS

| | | | |
|---|---|---|---|
| 3,510,923 | 5/1970 | Blake | 24/528 |
| 3,916,908 | 11/1975 | Leveen | 128/346 |
| 4,088,313 | 5/1978 | Pearson | 269/166 |
| 4,440,170 | 4/1984 | Golden et al. | 128/325 |
| 4,487,205 | 12/1984 | Di Giovanni et al. | 128/346 |
| 4,490,326 | 12/1984 | Beroff et al. | 128/346 |
| 4,527,562 | 7/1985 | Mericle | 128/346 |
| 4,555,100 | 11/1985 | Ditto | 269/166 |

FOREIGN PATENT DOCUMENTS 72232 2/1983 European Pat. Off. ............ 128/346

*Primary Examiner*—Robert Peshock
*Assistant Examiner*—John G. Weiss
*Attorney, Agent, or Firm*—Charles F. Costello, Jr.

[57] ABSTRACT

A nonmetallic surgical clip having two separate and noncontiguous parts is decribed. Each part contains an arm, and means for approximating the cooperating surfaces of the two arms. The clip is useful in ligating a blood vessel, e.g. an artery.

11 Claims, 8 Drawing Figures

NONMETALLIC SURGICAL CLIPP

BACKGROUND OF THE INVENTION

This invention relates to a nonmetallic surgical clip. More specifically, this invention relates to a nonmetallic surgical clip having two separate and noncontiguous parts. Each part of the clip contains an arm, and means for approximating the cooperating surfaces of the two arms.

An embodiment of this invention is wherein the approximating means comprise a protrusion at the proximal end of one arm and an opening at the proximal end of the other arm. A specific embodiment is wherein the protrusion and the opening are in an oblique relationship to the arms.

The oblique relationship of the protrusion and the opening to the arms has at least two advantages. One advantage is that the height of the surgical clip decreases in an oblique relationship between the protrusion and the opening, and the arms, as compared to a perpendicular relationship. Also the greater the oblique relationship (that is, the further from a perpendicular or 90° relationship), the greater the decrease in the height of the surgical clip.

Another advantage is that the force required to open a surgical clip after the cooperating surfaces have been approximated increases with an oblique relationship between the protrusion and the opening, and the arms, as compared to a perpendicular relationship. Again, the greater the oblique relationship (that is, the further from a perpendicular or 90° relationship), the greater the increase in the force required to open a surgical clip.

Both of these advantages are extremely important, and may even be critical, in a surgical procedure, e.g. the ligating of a blood vessel. It is critical that a surgical ligating clip stop the flow of blood through a vessel. If the vessel ligated is an artery, then a variable force (due to the expansion and contraction of the heart muscle) will be acting on the clip. The surgical clip of this invention in an oblique relationship assures a wide margin of safety against even a partial opening of the approximated clip cooperating surfaces, after a blood vessel is ligated.

Also of extreme importance is the size of the surgical clip and mechanical applicator used in ligation. That is, surgical clips, although ideal in all properties except size, can be essentially without usefulness if, e.g., the vessel or tissue to be ligated is in a small area or if other vessels or organs impede the placement of the applicator and/or clip. Therefore, as a general statement, a better surgical clip is one that is smaller and/or thinner than the state of the art surgical clips. For all of the above reasons, the surgical clip of this invention is new, useful and unobvious over the known state of the art surgical clips.

SUMMARY OF THE INVENTION

A nonmetallic surgical clip having two separate and noncontiguous parts has been invented. Each part contains an arm, and means for approximating the cooperating surfaces of the two arms.

In one embodiment, the nonmetallic material is bioabsorbable. In another embodiment, the bioabsorbable material is a synthetic polymer. In still another embodiment, the synthetic polymer has a glycolic acid ester linkage. In yet another embodiment, the polymer having a glycolic acid ester linkage is a homopolymer. In still yet another embodiment, the polymer having a glycolic acid ester linkage is a copolymer. As a specific embodiment, the copolymer has a glycolic acid ester linkage and a trimethylene carbonate linkage.

In a further embodiment, the arms of the surgical clip are in an essentially mirror-image relationship.

In a still futher embodiment, the cooperating surfaces of the arms are in an essentially parallel relationship. In yet a further embodiment, one of the cooperating surfaces of the arms contains a raised portion.

In a more specific embodiment, at least a portion of the other cooperating surface is serrated.

Also, an embodiment is wherein the approximating means comprise a protrusion at the proximal end of one arm and an opening at the proximal end of the other arm. A specific embodiment is wherein the protrusion and the opening are in an oblique relationship to the arms.

A more specific embodiment is wherein the approximating means contain means for dovetailing; the dovetailing means are adjacent the proximal end of the protrusion. A still more specific embodiment is wherein the dovetailing means comprise a mortise.

DESCRIPTION OF THE INVENTION

Figure 1:
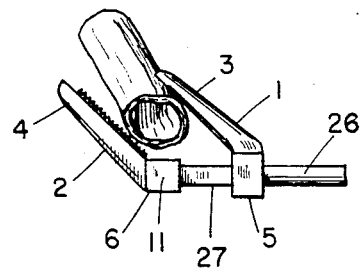
FIG. 1 is a side view of the surgical clip of this invention prior to the approximation of a blood vessel.

FIGS. 1 to 7 describe a surgical ligating clip having two separate and noncontiguous parts 1 and 2. Each part comprises an arm 3 and 4, respectively. Each part also comprises a means 5 and 6, respectively, for approximating the cooperating surfaces (see,e.g., element 8 in FIG. 6) of the two arms 3 and 4. Referring to FIGS. 1 and 2, 4 and 5, or 6 and 7, the relationship of the approximating means 5 and 6 to the arms 3 and 4 is preferably an oblique relationship.

Figure 4:
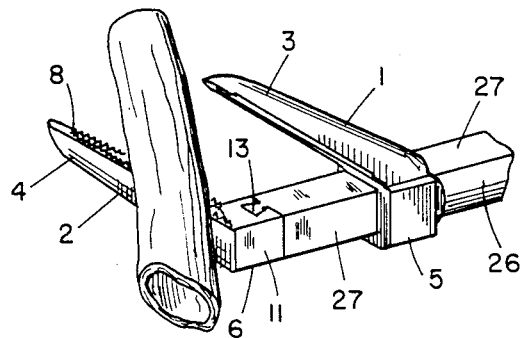
FIGS. 4 and 5 are perspective views of FIGS. 1 and 2, respectively.
Figure 6:
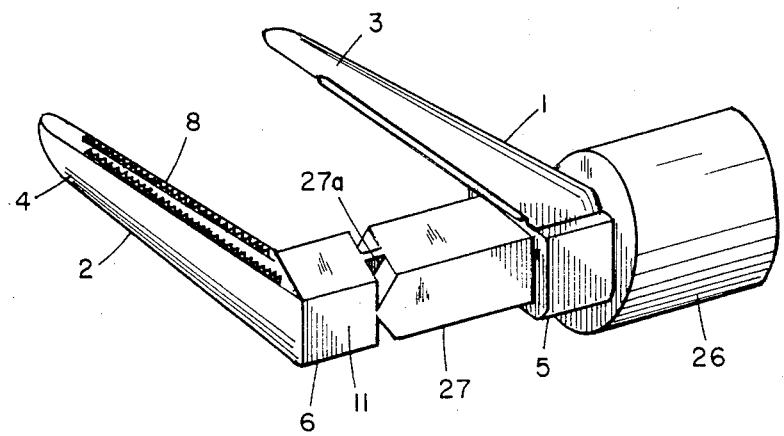
FIG. 6 is a perspective view of the surgical clip of this invention showing a means for attaching one part of the surgical clip to a mechanical applicator.

Referring to FIGS. 1, 4, and 6, the arms 3 and 4 are in an essentially parallel relationship. The cooperating surface of arm 3 can contain a raised portion. The cooperating surface 8 of arm 4 is at least partially serrated. The approximating means 6 can comprise a protrusion 11 at the proximal end of arm 4.

Figure 2:
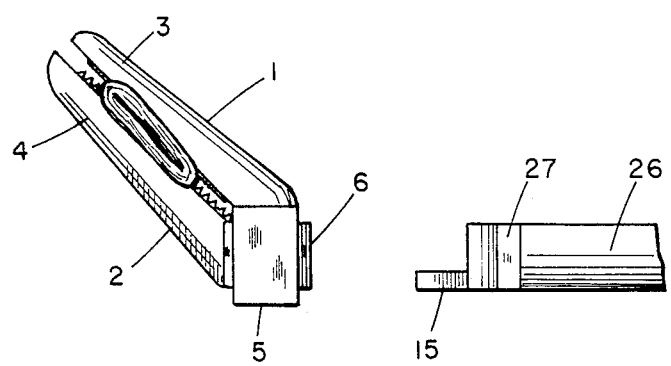
FIG. 2 shows the surgical clip of this invention after approximation of the blood vessel shown in FIG. 1.
Figure 5:
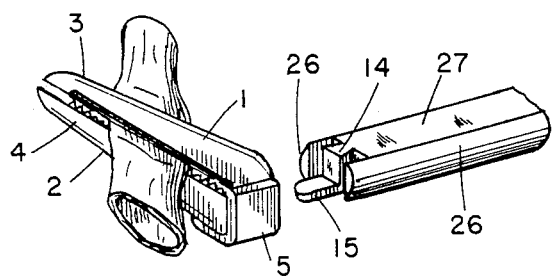
Figure 7:
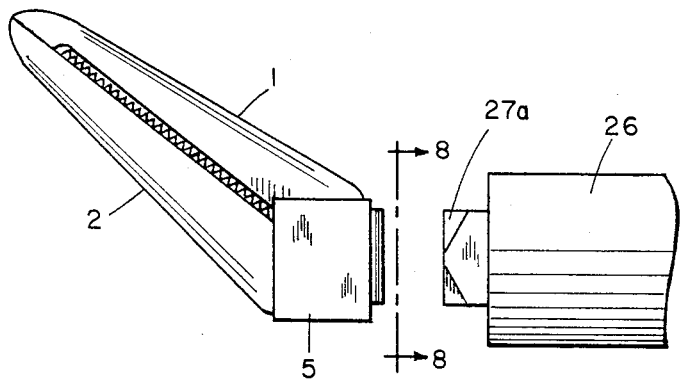
FIG. 7 is a side view of the surgical clip of FIG. 6, after the clip cooperating surfaces have been approximated.

As implicitly shown in FIGS. 2, 5 and 7, the approximating means 5 can comprise an opening. The arms 3 and 4 are approximated by fitting the protrusion 11 into the opening.

Referring to FIGS. 1 and 4, the protrusion 11 has a geometrical configuration essentially identical in shape but a cross-sectional perimeter slightly smaller than the inside perimeter of the approximating means 5 opening. Further, to assure a more permanent contact, the protrusion 11 can have a taper and the opening in the approximating means 5 can have an approximately equal reverse taper.

The protrusion 11 can be inserted, either manually or with a mechanical applicator, into the approximating means 5 opening. A mechanical applicator is preferred. FIGS. 1 to 5 and 6 to 8 show alternative distal ends of applicators which can be used to mechanically approximate the cooperating surfaces of arms 3 and 4.

In these figures, the surgical clip arms tend to be more than 90° away fom the distal end of the mechanical applicators. However, it is to be understood that the surgical clip arms can be less than 90° away from the distal end of the mechanical applicators.

Referring to FIGS. 1 to 3 or 4 and 5, if a mechanical applicator is used, the approximating means 6 can contain a means for dovetailing the protrusion 11 onto the mechanical applicator. The dovetailing means can comprise a mortise 13 on the protrusion 11 and a tenon 14 on the mechanical applicator.

The approximating means 5 can be movable contained on the mechanical applicator. To accomplish this, the mechanical applicator can have a shaft 27. As shown, e.g., in FIG. 4, the cross-sectional perimeter of the shaft 27 is essentially identical to the approximating means 5 opening. Also, the cross-sectional area of the shaft 27 is slightly less than the cross-sectional area of the approximating means 5 opening. The actual differences between these cross-sectional areas is not critical provided that a force applied to the approximating means 5 can overcome the static friction between the contact surfaces of the shaft 27 and the approximating means 5 opening.

Figure 3:
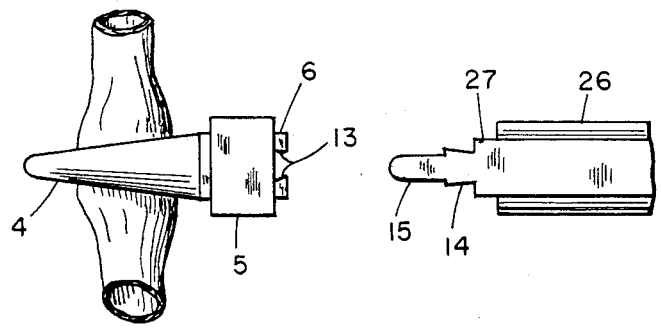
FIG. 3 is a bottom view of FIG. 2.

The approximating means 6 can also contain a slot forward of and below the mortise 13. Referring to FIGS. 2, 3, and 5 the shaft 27 can contain a tab 15. The tab 15 is placed into the approximating means 6 slot during dovetailing of the protrusion 11 to the mechanical applicator. This prevents the ligating clip part 2 from disengaging from the applicator (e.g., as shown in FIGS. 1 and 4, during ligation of a tubular vessel).

Figure 8:
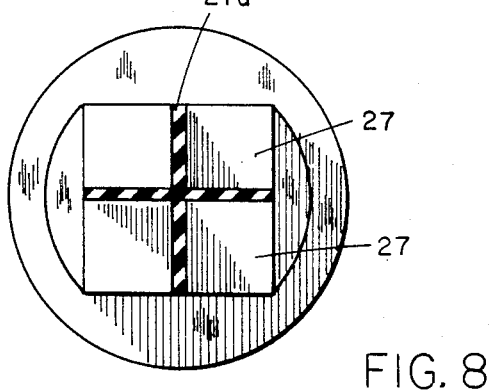
FIG. 8 is a front view of the mechanical applicator shown in FIGS. 6 and 7, taken along the plane 8—8 of FIG. 7.

Referring to FIGS. 6 to 8, a means for attaching the approximating means 6 to the shaft 27, and an alternative means for preventing disengagement of the ligating clip part 2 from a mechanical applicator is shown. The distal end of the shaft 27 is notched to obtain a weakened area 27a. Impliedly in this embodiment, the part 2 and the shaft 27 are manufactured from a sole piece of nonmetallic material, e.g. by machining or by injection molding. As shown in FIGS. 6 to 8, although the weakened portion 27a, is in the vertical, it is to be understood that the weakened portion can be any geometrical design, provided that the part 2 can be manually separated from the shaft 27 after the arms 3 and 4 are approximated.

The ligating clip of this invention can be mechanically applied to a living mammalian tissue, e.g. a tubular member such as a uterine artery. The application can be by a mechanical applicator. The type of mechanical applicator is not critical to the practice of this invention. That is, an applicator from the prior art can be used to apply the ligating clip to a living mammalian tissue. Examples of prior art applicators which can be used include, but are not limited to, a push-pull type, such as a plunger or piston device, and a fulcrum type, such as a medical device having scissors-like or pliers-like handles.

A push-pull applicator, such as a plunger can be used by pushing down on the plunger, for example, with the thumb. This causes the approximating means of part 1 to be engaged with the approximating means of the other part 2.

Referring to FIGS. 1 and 4 to 7, at the distal end of the plunger, part 2 of the clip is attached to a stationary member, for example interior rod 27. Part 1 of the clip is movably contained on the rod 27. The means for moving the clip part 1 (on the rod 27) can be an exterior rod 26. Referring to FIGS. 6 to 8, the exterior rod 26 can completely encircle the interior rod 27, or altenatively referring to FIGS. 1 to 5, there can be a pair of exterior rods 26 (see specifically FIG. 5). The pair of exterior rods 26 are positioned on opposite sides of the interior rod 27. The plunger can then be disengaged from the clip, for example by a latching means, or by a dovetailing means described above, after the cooperating surfaces of parts 1 and 2 have occluded a blood vessel or flattened a tubular member. Referring to FIGS. 2, 3 and 5, the force necessary to pull the tenon 14 from the mortise 13 is greater than the force necessary to occlude the largest blood vessel the clip can contain.

A fulcrum type applicator can be used, e.g., by bringing the two scissors-like handles together. This causes the approximating means of part 1 to be engaged with the approximating means of the other part 2. Referring to FIGS. 1 and 4 to 7, the distal end of the fulcrum type applicator can be essentially identical to that described above for the push-pull applicator. As examples of prior art fulcrum type surgical clip applicators which can be adapted without undue experimentation to engage clip parts 1 and 2, see U.S. Pat. Nos. 4,325,376, issued Apr. 20, 1982 and 4,242,902 issued Jan. 6, 1981. Both of these patents are incorporated herein by reference.

I claim:

1. A bioabsorbable nonmetallic surgical clip having two separate and noncontiguous parts, each part containing an arm, each arm having a surface for cooperating with the other arm, and means for approximating the cooperating surfaces of the two arms, the means for approximating comprising a protrusion at the proximal end of one arm and an opening at the proximal end of the other arm wherein said protrusion and opening are in an oblique relationship to said arms.

2. A clip of claim 1 wherein the bioabsorbable material is a synthetic polymer.

3. A clip of claim 2 wherein said polymer has a glycolic acid ester linkage.

4. A clip of claim 3 wherein said polymer is a homopolymer.

5. A clip of claim 3 wherein said polymer is a copolymer.

6. A clip of claim 5 wherein said copolymer has a trimethylene carbonate linkage.

7. A clip of claim 3 wherein the said arms are in an essentially symmetrical relationship.

8. A clip of claim 3 wherein the cooperating surfaces of said arms are in an essentially parallel relationship.

9. A clip of claim 8 wherein one of the cooperating surfaces of said arms contains a raised portion.

10. A clip of claim 9 wherein at least a portion of the other cooperating surface is serrated.

11. A clip of claim 8 wherein the means for approximating comprise a mortise, said mortise being adjacent the proximal end of said protrusion.

* * * * *